(12) United States Patent
Lane

(10) Patent No.: US 6,187,811 B1
(45) Date of Patent: Feb. 13, 2001

(54) METHODS FOR TREATING BENIGN PROSTATIC HYPERPLASIA USING TOCOTRIENOLS

(75) Inventor: Ronald H. Lane, Phoenix, AZ (US)

(73) Assignee: LipoGenics, Inc., Phoenix, AZ (US)

(*) Notice: Under 35 U.S.C. 154(b), the term of this patent shall be extended for 0 days.

(21) Appl. No.: 09/182,115

(22) Filed: Oct. 28, 1998

(51) Int. Cl.⁷ .................................................. A61K 31/355
(52) U.S. Cl. ........................................ 514/458; 424/195.1
(58) Field of Search .......................... 424/195.1; 514/458

(56) References Cited

U.S. PATENT DOCUMENTS

| | | | |
|---|---|---|---|
| 3,064,012 | 11/1962 | Folkers et al. | 260/345.5 |
| 3,122,565 | 2/1964 | Kijima et al. | 549/413 |
| 4,603,143 | 7/1986 | Schmidt | 514/458 |
| 4,788,304 | 11/1988 | Marshall et al. | 549/549 |
| 5,034,420 | 7/1991 | Wang | 514/680 |
| 5,138,075 | 8/1992 | Ohgaki et al. | 549/413 |
| 5,204,373 | 4/1993 | Pearce | 514/720 |
| 5,217,992 | 6/1993 | Wright et al. | 514/458 |
| 5,296,508 | 3/1994 | Pearce | 514/510 |
| 5,348,974 | 9/1994 | Wright et al. | 514/456 |
| 5,393,776 | 2/1995 | Pearce | 514/486 |

FOREIGN PATENT DOCUMENTS

| | | |
|---|---|---|
| 3221506 | 12/1983 | (DE) . |
| 304842 | 3/1989 | (EP) . |
| 421419 | 4/1991 | (EP) . |
| 870638 | 6/1961 | (GB) . |
| 1011319 | 11/1966 | (GB) . |
| 1506076 | 4/1978 | (GB) . |
| 2264712 | 10/1990 | (JP) . |

OTHER PUBLICATIONS

Patent Abstracts of Japan, vol. 9, No. 91 (C–277)(1814) Apr. 19, 1958 of JP, A, 59 222 414 (Kuraray) Dec. 12, 1984.

Qureshi et al., "The Structure of an Inhibitor of Cholesterol Biosynthesis isolated from Barley," *Journal of Biological Chemistry* vol. 261, No. 23 (1986) pp. 10544–10550.

Schudel et al., "Über die Chemie des Vitamins E," *Helvetica Chimica Acta* vol. 46, No. 281 (1963) 2517–2526.

*Primary Examiner*—Jean C. Witz
(74) *Attorney, Agent, or Firm*—Lyon & Lyon LLP

(57) ABSTRACT

This invention relates to the treatment of benign prostatic hyperplasia (BPH) using tocotrienols. Specifically, this invention relates to compositions and the use of compositions comprising individual tocotrienols, mixtures of tocotrienols and mixtures of one or more tocotrienols with other anti-BPH substances.

10 Claims, No Drawings

US 6,187,811 B1

METHODS FOR TREATING BENIGN PROSTATIC HYPERPLASIA USING TOCOTRIENOLS

TECHNICAL FIELD OF THE INVENTION

This invention relates to the treatment of benign prostatic hyperplasia (BPH) using tocotrienols. Specifically, this invention relates to compositions and the use of compositions comprising individual tocotrienols, mixtures of tocotrienols and mixtures of one or more tocotrienols with other anti-BPH substances.

BACKGROUND OF THE INVENTION

It is estimated that over half of men over age 50 and three quarters of men over age 70 experience benign prostatic hyperplasia (BPH). BPH is a condition characterized by a swelling of the prostate; the gland is responsible for secreting an alkaline fluid that is incorporated in seminal fluid. The prostate gland is located below the bladder and surrounds part of the urethra. While prostate enlargement is regarded as a normal part of aging, BPH progression can cause a number of lower urinary tract symptoms and related complications. As the prostate swells, the urethra becomes constricted and obstructs the bladder. This obstruction leads to many of the symptoms of BPH: painful urination, decreased flow, difficulty starting or stopping flow, nocturnal urination, incomplete voiding and others. Complications such as recurrent urinary tract infections, pyelonephritis, chronic and acute urinary retention, dilatation and hydronephrosis can also occur. In some cases, BPH has also been linked to chronic and acute renal failure.

There are two general approaches to addressing BPH: drug treatment and surgery. Currently available drug treatments include the use of alpha-blockers, hormonal therapeutics and herbal medicines. Alpha-blockers relax smooth muscle by selectively blocking alpha-1 adrenoreceptors in the bladder neck and prostate, thereby relieving some of the symptoms associated with BPH. This class includes drugs such as prasozin, doxazosin, indoramin, asfuzasin, terazosin and tamsulosin. Disadvantages of the alpha-blockers include frequency of dosing, side effects and cost. Hormonal therapeutics are anti-androgens that prevent certain hormonal changes involved with BPH. Finasteride (Proscar®, Merck & Co., Inc.) is the leading drug of this class. It prevents the production of dihydrotestosterone (DHT), an androgen that accumulates within the prostate and causes the prostatic enlargement associated with BPH. Finasteride acts by specifically inhibiting steroid 5-alpha reductase, an enzyme responsible for converting testosterone into DHT. Although relatively free from side effects, finasteride is expensive and has a much slower onset of action than the alpha-blockers.

Herbal medicines are a popular alternative to synthetic drugs for treating BPH. These include phytosterols (e.g., beta-sitosterol), saw palmetto berry extracts, Pinus extracts, Picea extracts, Hypoxis extracts, Redix urticae extracts, pumpkin seed extracts (such as cubicin), pygeum, ginseng, cayenne (capsicum), goldenseal root and pollen extracts (such as cernilton).

Despite the existence of these therapeutic options, surgery remains the most effective method of treating BPH, particularly in cases of acute and chronic retention. Surgical methods include transurethral resection of the prostate, transurethral incision, thermotherapy, stents and ultrasound. However, the inherent dangers of surgery, the frequency of post-operative morbidity and the likelihood of needing repeat procedures make surgery an undesired option.

Accordingly, there is still a well-recognized and unmet need for new agents to treat benign prostatic hyperplasia.

SUMMARY OF THE INVENTION

The present invention satisfies the need for new therapeutic agents effective in the treatment of benign prostatic hyperplasia.

One embodiment of this invention provides a method for treating benign prostatic hyperplasia in a patient comprising the step of administering to the patient a therapeutically effective amount of a composition comprising a tocotrienol, a mixture of tocotrienols or a combination of one or more tocotrienols with one or more additional anti-BPH substances.

Another embodiment of this invention provides novel compositions comprising a combination of one or more tocotrienols with one or more additional anti-BPH substances.

DETAILED DESCRIPTION OF THE INVENTION

As used herein, the following definitions apply (unless expressly noted to the contrary):

"anti-BPH" refers to agents or substances that have a beneficial effect on the cause or symptoms of BPH either alone or in combination with a tocotrienol or mixture thereof. Preferably, these anti-BPH substance and agents are selected from alpha-blockers, anti-androgens (such as steroid 5-alpha reductase inhibitors), herbal medicines and anti-inflammatory agents. More preferably, these anti-BPH substances and agents are selected from the group of alpha-blockers consisting of prasozin, doxazosin, indoramin, asfuzasin, terazosin and tamsulosin; the anti-androgen, finasteride, the group of herbal medicines (including a part or extract thereof, as appropriate) consisting of phytosterols (such as sitosterol (such as beta-sitosterol), sitosterol esters (such as fatty acid esters of sitosterol), sitostanol (such as beta-sitostanol), sitostanol esters (such as fatty acid esters of sitostanol), avenasterol, D-5 avenasterol, D-7 avenasterol, brassicasterol, 22,23-dihydobrassiccasterol, ergosterol, desmosterol, poriferasterol, sargasterol, fucosterol, chaunasterol, campesterol, D-7 campesterol, campesto-3,5-dienol, campostanol, cholesterol, 24 M cholesterol, 9,19 cyclolanosterol, 24 M-9,19 cyclolanosterol, stigmasterol, D-5,24 stigmasterol, D-7 stigmaterol, stigmasta-3 enol +1S, stigmasta-3,5 dienol and stigmasta-3,5,22 trienol), other plant unsaponifiables (such as ferulic acid, ferulic acid esters (e.g., ferulic acid esterified with triterpene alcohols, sterols and methanol), sterol esters (such as 4-methyl sterols), triterpene alcohols (such as cycloartanol, B-amyrin, cycloartenol, 24-methylene cycloartanol and cyclobranol), oryzanols (such as gamma-oryzanol), hydrocarbons (such as squalene) and carotenoids(such as beta carotene)), saw palmetto berry, Pinus, Picea, Hypoxis, Redix urticae, conjugated linoleic acid (including cis-9, cis-11-octadecadienoic acid, cis-9, trans-11-octadecadienoic acid, trans-9, cis-11-octadecadienoic acid, trans-9, trans-11 -octadecadienoic acid, cis-10, cis-12-octadecadienoic acid, cis-10, trans-12-octadecadienoic acid, trans-10, cis-12-octadecadienoic acid, trans-10, trans-12-octadecadienoic acid and other stable isomers thereof), tocopherols (alpha-, beta-, gamma-, or delta-tocopherol), pumpkin seed (including cubicin), pollen (including cernilton), ginseng (e.g., Chinese and Siberian), juniper berry, Urtica droica L.and urens L., pygeum (including *Pygeum africanum*), goldenseal, gravel root, hydrangea, sea holly, kelp, garlic, marshmallow leaves, horsetail, cayenne (capsicum) and false unicorn root and conventional anti-inflammatory agents (such as non-steroidal anti-inflammatory agents (e.g., aspirin, naproxen salts and ibuprofen)). Most preferably, the anti-BHP agents useful in this invention are selected from the group consisting of saw palmetto berry, Pinus, Picea, Hypoxis, Redix urticae, conjugated linoleic acid, pumpkin seed, pollen, ginseng, juniper berry, Urtica droica L., Urtica urens L., pygeum, goldenseal, gravel root, hydrangea, sea holly, kelp, garlic, marshmallow leaves, horsetail, cayenne and false unicorn root and extracts thereof. The markers and tests for measuring the anti-BPH activities of such agents are well established in the art. In addition to the anti-BHP agents listed above, the use of tocopherols (preferably, alpha-, beta-, gamma-, or delta-tocopherol) and conventional non-steroidal anti-inflammatory agents (such as aspirin, naproxen salts and ibuprofen) is also preferred in the methods of this invention.

"Composition" as used herein refers to a preparation for administration via any acceptable route known to those of ordinary skill in the art. Such routes include, but are not limited to oral, nasal, inhalational, parenteral, intravenous and topical administration. "Composition" encompasses pharmaceutical compositions as well as dietary supplements, foodstuffs, food additives and the like.

"Patient" refers to a warm-blooded mammal and preferably, a human. Patients in need of treatment for BPH are those patients possessing one or more symptoms of BPH or related complications, including painful urination, decreased flow, difficulty starting or stopping flow, nocturnal urination, incomplete voiding, recurrent urinary tract infections, pyelonephritis, chronic and acute urinary retention, dilatation and hydronephrosis.

"$P_{18}$ tocotrienol" refers to a tocotrienol having the formula

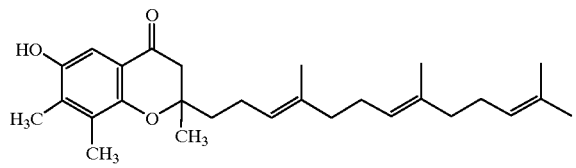

$P_{18}$ tocotrienol and $P_{18}$ are trademarks of Bionutrics, Inc. (Phoenix, Ariz.).

"$P_{25}$ tocotrienol" refers to the tocotrienol 3,4-dihydro-2-(4,8,12-trimethyltrideca-3'(E),7'(E), 11''-trienyl)-2H-1-benzopyran-6-ol) which has the formula

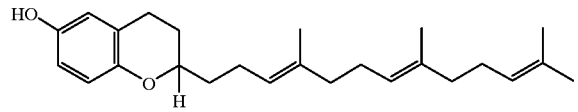

This compound is also known as didesmethyl-tocotrienol in some of the literature cited herein. $P_{25}$ tocotrienol and $P_{25}$ are trademarks of Bionutrics, Inc. (Phoenix, Ariz.).

"Therapeutically acceptable amount" refers to an amount of active ingredient sufficient to treat or reduce the severity of the symptoms of BHP in a patient in need of such treatment. "Therapeutically acceptable means" refers to means effective to impart a measurable therapeutic effect.

"Tocotrienol", when used to refer to a specific compound, refers to the compound 3,4-dihydro-2-methyl-2-(4,8,12-trimethyltrideca-3'(E), 7'(E), 11''-trienyl)-2H-benzopy-6-ol. When used generally to describe the class of compounds, the definition set forth below will apply.

"Tocotrienol", when used in the general sense, refers to compounds possessing the following three structural characteristics: (1) a hydrogen donor group (or a group that can be hydrolyzed to a hydrogen donor group) attached to an aromatic ring system; (2) a side chain attached to the aromatic ring system comprising one or more isoprenoid or isoprenoid-like units and (3) a methylene unit or a functional group having at least one lone pair of electrons positioned adjacent to the atom to which the side chain is attached to the aromatic ring system, said electrons being conjugated to the aromatic ring system (preferably $CH_2$, C=O, CHOH, O, S or NH). Specific isoprenoid-like units include truncated isoprenoids and truncated or full-length isoprenoids that may be or may not be partially saturated and are optionally substituted with OH, $NH_2$ and $C_1$–$C_6$ branched or unbranched alkyl or alkoxy. Preferred tocotrienols for use in the methods of this invention are those which are naturally occurring (including tocotrienol, α-, β-, γ-, δ-tocotrienol, $P_{25}$ and $P_{18}$) and may be used individually or in combination. These naturally occurring tocotrienols may be conveniently isolated from biological materials or synthesized from commercially available starting material. Preferably, the tocotrienols for use in the methods of this invention are obtained from biological materials that have been stabilized and extracted, such as by the processes described in PCT publication WO 91/17985 (the entire disclosure of which is hereby incorporated by reference). Examples of preferred biological materials, tocotrienols and methods for obtaining tocotrienols synthetically and from biological materials are referred to in co-owned U.S. Pat. No. 5,591,772 and PCT publication WO 91/17985 (the entire disclosures of which are hereby incorporated by reference). Preferred biological materials from which the some of the preferred tocotrienols useful in the compositions and methods of this invention may be obtained include those from conifers, legumes, asteraceae, poaceae and palmae and more specifically, tocotrienol-rich extracts from stabilized brans (especially, stabilized rice bran), psyllium seed, barley, pine nut, sunflower, peanut, palm fruit, millet, avacado, juniper berries, cedar leaves, mango, pine needles, rubber tree leaves, tomato and amaranth. In addition to the tocotrienols described above, the term "tocotrienol" also includes the farnesylated tetrahydro-naphthalenols and monocyclic tocotrienol analogs described (both generically and specifically) in U.S. Pat. Nos. 5,204,373 and 5,393,776.

Specific preferred tocotrienols of this invention include those of formula (I):

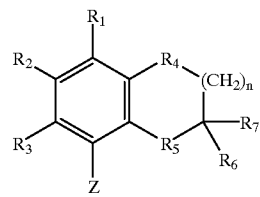

wherein
$R_1$ and $R_3$ are each independently selected from the group consisting of H, halogen, OH, $OCH_3$ and $C_1$–$C_6$ branched or unbranched alkyl (preferably, H, halogen and $C_1$–$C_3$ branched or unbranched alkyl and more preferably, H and methyl);
$R_2$ is selected from the group consisting of halogens (preferably, chlorine) and hydrogen donor group selected from the group consisting of OH, $NHR_8$, $CO_2Y$, $C(R_8)_2CO_2H$ and $C_1$–$C_8$ branched or unbranched alkyl substituted with OH, $NHR_8$, $CO_2Y$ or $C(R_8)_2CO_2H$ (preferably, OH and $C_1$–$C_3$ branched or unbranched alkyl substituted with OH and more preferably, OH);

$R_4$ is selected from the group consisting of O, NH, CH—$R_9$, C=O and CH—OH (preferably, O, $CH_2$ and C=O);

$R_5$ is selected from the group consisting of $CH_2$, C=O, CHOH, O, S and NH (preferably, O, $CH_2$ and C=O and more preferably, O and C=O);

$R_6$ is selected from the group consisting of H and $C_1$–$C_6$ branched or unbranched alkyl (preferably, H and $C_1$–$C_3$ branched or unbranched alkyl and more preferably, H and methyl);

$R_7$ is selected from the group consisting of isoprenoid and isoprenoid-like side chains, and more preferably from the group consisting of side chains of formulas (a)–(c):

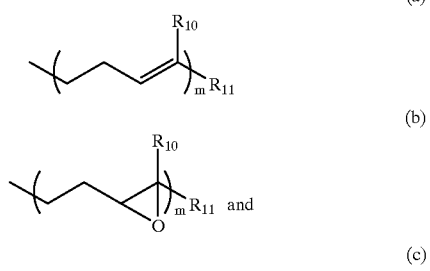

and also includes combinations of one or more of the repeating units shown in side chains (a)–(c), and, if the repeating unit shown in side chain (a) is present one or more unsaturated analogs thereof, or if the repeating unit in side chain (c) is present, one or more oxidized analogs thereof (including keto and dione analogs thereof) and wherein each $R_{10}$ is independently selected from the group consisting of H, OH, $NH_2$ and $C_1$–$C_6$ branched or unbranched alkyl or alkoxy and $R_{11}$ is selected from the group consisting of H, $C_1$–$C_6$ branched or unbranched alkyl or alkoxy, $CH_2OH$, $CO_2H$ (and $C_1$–$C_6$ alkyl esters thereof) and OH (preferably, $R_7$ is a side chain of formula (a), wherein $R_{10}$ and $R_{11}$ are each independently is selected from the group consisting of H and $C_1$–$C_3$ branched or unbranched alkyl and more preferably, H and methyl);

each $R_8$ and $R_9$ is independently selected from the group consisting of H and $C_1$–$C_6$ branched or unbranched alkyl (preferably, H and $C_1$–$C_3$ branched or unbranched alkyl and more preferably, H and methyl);

Y is H or and $C_1$–$C_{18}$ branched or unbranched alkyl (preferably H and $C_1$–$C_6$ branched or unbranched alkyl and more preferably, H and $C_1$–$C_4$ branched or unbranched alkyl);

Z is selected from the group consisting of H, halogen, OH, $CH_2OH$, $CH_3$, $OCH_3$ and $COCH_3$ (preferably H and $CH_3$);

n is an integer selected from the group consisting of 0, 1, 2, 3 and 4 (preferably 0 and 1); and m is an integer selected from the group consisting of 1–30 (preferably 1–20, more preferably 3–10 and most preferably, 3–7).

More preferred tocotrienols of this invention include tocotrienol, α-tocotrienol, β-tocotrienol, γ-tocotrienol, δ-tocotrienol, $P_{18}$ tocotrienol and $P_{25}$ tocotrienol.

This invention expressly encompasses the prodrug form of tocotrienols. Upon administration to a patient, such a prodrug undergoes biotransformation to their active form. Prodrugs include the esterified form of the tocotrienols used in this invention which comprise a carboxylic acid functionality.

The tocotrienols for use in the compositions and methods of this invention may be in their isomerically pure form or be present as mixtures of isomers. For example, the tocotrienols of this invention may exist as the d- or l-isomer or the d,l-racemic mixture. The naturally occurring isomer (usually the d-isomer) and the d,l-racemic mixture are preferred.

"TRF" refers to a tocotrienol rich fraction obtained by the stabilization and extraction of a biological source. Preferred TRF is obtained from brans (especially, stabilized rice bran), psyllium seed, barley, pine nut, sunflower, peanut, palm fruit, millet, avacado, juniper berries, cedar leaves, mango, pine needles, rubber tree leaves, tomato and arnaranth.rice bran or rice bran oil. More preferably, the TRF is obtained from rice bran. TRF typically contains varying amounts of $P_{21}$ tocotrienol, α-tocotrienol, β-tocotrienol, γ-tocotrienol and δ-tocotrienol and may also contain quantities of the newly discovered tocotrienols, $P_{18}$ tocotrienol and $P_{25}$ tocotrienol. Most commonly, TRF will comprise at least about 0.5% tocotrienols w/w (preferably, at least about 1%, more preferably 1.5%, even more preferably 2%). Preferred TRFs may also comprise tocopherols (such as α-, β-, γ- and δ-tocopherol), plant sterols (including but not limited to sitosterol (such as beta-sitosterol), sitosterol esters (such as fatty acid esters of sitosterol), sitostanol (such as beta-sitostanol), sitostanol esters (such as fatty acid esters of sitostanol), avenasterol, D-5 avenasterol, D-7 avenasterol, brassicasterol, 22,23-dihydobrassiccasterol, ergosterol, desmosterol, poriferasterol, sargasterol, fucosterol, chaunasterol, campesterol, D-7 campesterol, campesto-3,5-dienol, campostanol, cholesterol, 24 M cholesterol, 9,19 cyclolanosterol, 24 M-9,19 cyclolanosterol, stigmasterol, D-5,24 stigmasterol, D-7 stigmaterol, stigmasta-3 enol +1S, stigmasta-3,5 dienol and stigmasta-3,5,22 trienol), other plant unsaponifiables (such as ferulic acid, ferulic acid esters (e.g., ferulic acid esterified with triterpene alcohols, sterols and methanol), sterol esters (such as 4-methyl sterols), triterpene alcohols (such as cycloartanol, B-amyrin, cycloartenol, 24-methylene cycloartanol and cyclobranol), oryzanols (such as gamma-oryzanol), hydrocarbons (such as squalene) and carotenoids (such as beta carotene)), glycerols and free fatty acids. A preferred TRF has the following w/w composition: tocotrienols (about 0.1—about 25%; preferably, about 0.5—about 20%; more preferably, about 1—about 15%), tocopherols (about 0.1—about 25%; preferably, about 0.5—about 20%; more preferably, about 1—about 15%), (total tocotrienols+tocopherols (about 0.2—about 50%; preferably, about 1—about 40%; more preferably, about 2—about 30%)), plant sterols (about 0.1—about 50%; preferably, about 0.5—about 25%; more preferably, about 1—about 10%), other unsaponifiables (about 10—about 60%; preferably about 15—about 50%; more preferably, about 20—about 40%) and glycerols+free fatty acids (about 10—about 90%; preferably about 15—about 75%; more preferably about 20—about 60%). The individual tocotrienols in the tocotrienol component of the preferred TRFs are preferably within the following ranges (w/w): α-tocotrienol (about 0—about 40%; preferably, about 0—about 35%; more preferably, about 0—about 30%), β-tocotrienol (about 1—about 30%; preferably, about 1—about 25%; more preferably about 1—about 20%), γ-tocotrienol (about 10—about 90%; preferably, about 25—about 90%; more preferably; about 40—about 90%;) and δ-tocotrienol (about 1—about 30%;

preferably, about 1—about 20%; more preferably, about 1—about 10%).

Additional preferred TRFs include those produced by any of the methods described in co-pending U.S. patent application Ser. No. 08/583,232 (the disclosure of which is hereby incorporated by reference in its entirety).

"TRF$_{25}$" refers to a TRF comprising a significant weight percentage of P$_{25}$ tocotrienol. Preferably, TRF$_{25}$ comprises at least about 5% P$_{25}$, more preferably, at least about 10% P$_{25}$, and even more preferably, at least about 15% P$_{25}$ w/w. An example of the preparation of a specific TRF$_{25}$ is set forth in A. A. Qureshi et al., *Nutr. Biochem.*, 8, pp. 290–98 (1997). TRF$_{25}$ is a preferred component of the compositions and methods described herein. TRF and TRF$_{25}$ may be used in any of the methods and compositions described herein for individual tocotrienols or mixtures thereof.

All documents cited herein are hereby incorporated by reference in their entirety.

Without wishing to be bound by theory, tocotrienols are useful in treating BPH due to their unique combination of properties. As opposed to conventional therapeutics that target a single mechanism, tocotrienols target multiple mechanisms leading to and propagating BPH. For example, tocotrienols inhibit the production or activity of a variety of inflammatory cytokines and other pro-inflammatory factors (such as IL-1 and TNF-alpha). As a result of their unique combination of properties, tocotrienols are capable of combating the symptoms and, perhaps, the root causes of BHP.

Compositions of this invention are prepared by combining one or more tocotrienols with an acceptable carrier. For pharmaceutical compositions of this invention, the carrier must be pharmaceutically acceptable (i.e., a carrier which is non-toxic to the patient at the administered level and which does not destroy the activity of the active component(s) of the composition). Acceptable carriers, including pharmaceutically acceptable carriers, are well known to those of ordinary skill in the art.

The compositions of this invention may be used or administered by any therapeutically acceptable means to a patient. For example, pharmaceutical compositions of this invention may be administered orally, nasally, inhalationally, topically, transdermally, parenterally, intravenously or by inhalation. These compositions may be formulated so as to impart a time-released benefit. Oral compositions may take the form of tablets, capsules, caplets, emulsions, liposomes, suspensions, powders and the like. Topical compositions include, but are not limited to, gels, lotions and creams. Parenteral compositions take the form of sterile solutions and emulsions and the like. Intravenous compositions include, but are not limited to sterile solutions. The preferred route of administration is oral administration.

Dosage levels and requirements are well-recognized in the art and may be chosen by those of ordinary skill in the art from publicly available sources. Typically, dosage levels will range between about 0.1 and about 10,000 mg of a tocotrienol or mixture of tocotrienols per dose. Preferably, the range is between about 0.1 and about 5,000 mg (more preferable, between about 1 and about 1000 mg and most preferably, between about 10 to about 500 mg) of active ingredient per dose (typically, with dosing one to three times daily). Continuous dosing may be required over a period of time to obtain maximum benefit. Specific dosage and treatment regimens will depend upon factors such as the patient's overall health status, the severity and course of the patient's disorder or disposition thereto and the judgment of the treating physician. Higher or lower doses may be employed as needed.

Tocotrienols and mixtures thereof may be used in combination with the anti-BPH agents described herein. These additional agents may be administered separately from the tocotrienols or mixtures thereof, or they may be formulated together in a single dosage form. Such combination therapy may advantageously utilize lower dosages of each active component, avoid possible toxicity incurred when certain agents are used as monotherapies or may create an additive or synergistic effect. In a particularly preferred embodiment, one or more tocotrienols may be used in conjunction with one or more of the following anti-BPH agents: saw palmetto berry extract, β-sitosterol, tocopherols and conjugated linoleic acid.

EXAMPLES

In order that this invention be more fully understood, the following examples are set forth. These examples are for the purpose of illustration only and are not to be construed as limiting the scope of the invention in any way.

Methods used for obtaining and purifying tocotrienols and mixtures thereof (including TRF) useful for the methods of this invention are described in the Examples section of U.S. Pat. No. 5,591,772 and co-pending U.S. patent application Ser. No. 08/583,232. Stabilization of rice bran follows Example 1 of U.S. Pat. No. 5,591,772. TRF, TRF$_{25}$, P$_{25}$ tocotrienol and P$_{18}$ tocotrienol can be produced by following Examples 2–4 of U.S. Pat. No. 5,591,772. Other methods are known to those of skill in the art.

The following specific protocols can be used to produce rice bran oil from which tocotrienols and mixtures thereof can be isolated:

Protocol I: Dry Heat Stabilization
Extruder: Wenger Model X-25

Standard Screw/Barrel Setup

| Barrel No. | Standard Port | Screw No. | Standard Port |
|---|---|---|---|
| 5 | 28714-9 | 5 | 28320-1 |
| 4 | 28318-1 | 4 | 8326-9 |
| 3 | 28372-9 | 3 | 28326-1 |
| 2 | 28318-1 | 2 | 28326-1 |
| 1 | 28350-1 | 1 | 28387-9 |

Standard Die Setup

| Die/Spacer | Measurement | Standard Port |
|---|---|---|
| Spacer | 0.375 | 28340-11 |
| Back Plate | 0.625 | 28361-51 |
| Intermediate Plate | 0.218 | 28316-723 |
| Front Plate | 0.235 | 28389-507 |

Operating Conditions

| | |
|---|---|
| Feed Rate: | 1000 lbs/hr |
| Temperature: | 170° C. at exit die |
| Pressure: | 975–1025 psi |
| Moisture Feed: | 12% |
| Moisture Discharge: | 9.6% |
| Residence Time: | 15 seconds |
| Run Duration: | 8 hours |
| Sample Size: | 50 lbs |

Protocol II: Dry Heat Followed By Wet Heat Stabilization

Dry Heat Stage: Protocol I

Wet Heat Stage:

Extruder: Anderson 4 inch

Screw Barrel Configuration: Standard Cut Flight

Die Setup:

Diameter: 0.1875 inches
Length: 0.75 inches

Operating Conditions:

Feed Rate: 378 lbs/hr
Shaft Speed: 279 rpm
Steam Injection: 36 lbs/hr (32 psi at #8 hole)
Mechanical Pressure: 750 psi (ast.)
Moisture Feed: 11.4%
Discharge Moisture: 15%
Discharge Rate: 450 lbs/hr
Discharge Temp.: 121° C.

Protocol III: Drying/Cooling Procedure

The wet heat stabilized product of protocol II (15% moisture) was discharged onto aluminum trays and placed in a tray oven at 101.1° C. until the moisture content was 8–10% (approximately 1.5 hrs). The trays were then placed on tray racks and allowed to cool at ambient temperature (approximately 20° C.).

| Protocol IV: Oil Extraction | |
|---|---|
| Oil to Hexane Ratio: | 1:4 |
| No. of Washings: | 3 |
| Extraction Temperature | 40° C. |

The hexane was removed from the extract by mild heating (40° C.) under a mild vacuum.

Protocol V: Dewaxing 20 lbs of crude oil were refrigerated for 24 hrs at −15.6° C. The supernatant (containing the dewaxed oil) was decanted from the solidified waxes. The waxes were then centrifuged to removed entrained oil, yielding 0.59 lbs of waxes and 19.41 lbs of dewaxed oil.

While a number of embodiments of this invention have been described herein, it should be apparent that the basic constructions may be altered to provide other embodiments that utilize the compositions and methods of this invention. Therefore, it will be appreciated that the scope of this invention is to be defined by the appended claims, rather than by the specific embodiments that have been presented hereinabove.

What is claimed is:

1. A method for treating benign prostatic hyperplasia in a patient in need of such treatment comprising administering to the patient a therapeutically effective amount of a composition comprising one or more tocotrienols.

2. The method according to claim 1, wherein the one or more tocotrienols is selected from the group consisting of TRF, $TRF_{25}$, α-tocotrienol, β-tocotrienol, γ-tocotrienol, δ-tocotrienol, $P_{18}$ tocotrienol and $P_{25}$ tocotrienol.

3. The method according to claim 1 or 2, wherein the composition further comprises one or more anti-BPH agents.

4. The method according to claim 3, wherein the anti-BPH agent is selected from the group consisting of alpha-blockers and anti-androgens.

5. The method according to claim 3, wherein the anti-BPH agent is selected from the group consisting of saw palmetto berry, Pinus, Picea, Hypoxis, *Redix utricae*, conjugated linoleic acid, pumpkin seed, pollen, ginseng, juniper berry, *Urtica droica L., Urtica urens L.*, pygeum, goldenseal, gravel root, hydrangea, sea holly, kelp, garlic, marshmallow leaves, horsetail, cayenne and false unicorn root and extracts thereof.

6. The method according to claim 3, wherein the anti-BPH agent is selected from the group consisting of phytosterols, saw palmetto extract, conjugated linoleic acid, tocopherols and non-steroidal anti-inflammatory agents.

7. The method according to claim 6, wherein the phytosterol is selected from sitosterol, sitostanol and fatty acid esters thereof.

8. The method according to claim 1 or 2, wherein the composition is administered orally.

9. The method according to claim 8, wherein the composition comprises between about 0.1 and about 5000 mg of tocotrienol/dose.

10. The method according to claim 9, further comprising the step of administering to the patient one or more anti-BPH agents.

* * * * *